United States Patent [19]

Figueroa, Jr. et al.

[11] Patent Number: 4,960,764
[45] Date of Patent: Oct. 2, 1990

[54] OIL-IN-WATER-IN-SILICONE EMULSION COMPOSITIONS

[75] Inventors: Ramon Figueroa, Jr., Oxford; Bobby G. Harrison, Jr., East Norwalk; James P. SaNogueira, Newtown, all of Conn.

[73] Assignee: Richardson-Vicks Inc., Shelton, Conn.

[21] Appl. No.: 312,347

[22] Filed: Feb. 15, 1989

Related U.S. Application Data

[63] Continuation of Ser. No. 22,876, Mar. 6, 1987, abandoned.

[51] Int. Cl.$^5$ ............................................. A61K 31/695
[52] U.S. Cl. ..................................... 514/63; 514/938; 514/939
[58] Field of Search ........................... 514/63, 938, 939

[56] References Cited

U.S. PATENT DOCUMENTS

| | | | |
|---|---|---|---|
| 4,054,670 | 10/1977 | Buhler | 424/358 |
| 4,254,105 | 3/1981 | Fukuda | 424/170 |
| 4,311,695 | 1/1982 | Starch | 424/184 |
| 4,355,046 | 10/1982 | Süess | 514/63 |
| 4,370,319 | 1/1983 | Chapin et al. | 514/63 |

*Primary Examiner*—Leonard Schenkman
*Attorney, Agent, or Firm*—David K. Dabbiere; Douglas C. Mohl; Jack D. Schaeffer

[57] ABSTRACT

An oil-in-water-in-silicone fluid (o/w/s) emulsion composition comprising (a) a silicone fluid continuous phase, (b) an aqueous discontinuous phase comprising an oil-in-water (o/w) emulsion, and (c) an effective dispersing amount of dimethicone copolyol for dispersing (b) in (a).

6 Claims, No Drawings

OIL-IN-WATER-IN-SILICONE EMULSION COMPOSITIONS

This is a continuation of application Ser. No. 22,876, filed on Mar. 6, 1987, now abandoned.

BACKGROUND OF THE INVENTION

This invention relates to a multiphase (i.e., moisturizing characteristics. The multiphase emulsion composition is in the form of an oil phase/water phase/silicone fluid phase ("o/w/s multiple emulsion"). In addition to its skin moisturizing activity, the subject o/w/s multiple emulsion may be used as a base form for various products requiring an emulsified dispersion system such as cosmetic and topical drug formulations.

Single emulsion skin care preparations, such as lotions and creams, of the oil-in-water (o/w) type and water-in-oil (w/o) type are well known in the cosmetic art and are in daily use by consumers, the o/w type being more commonly utilized. Multiphase (i.e., double) emulsion compositions, such as the water-in-oil-in-water (w/o/w) type, for example see U.S. Pat. No. 4,254,105, and the oil-in-water-in oil (o/w/o) type, are of lesser commercial significance to date in the cosmetic field. In general, such single or multiphase emulsions contain water, emollients and emulsifiers as essential ingredients and cosmetically acceptable optional additives such as preservatives, antioxidants, skin conditioners, humectants, thickeners, cleansers, colorants, odorants and other components generally utilized in the cosmetic art.

To date, applicants are unaware of a skin moisturizing multiphase emulsion composition of the o/w/s type wherein "s" consists essentially of a silicone fluid. In U.S. Pat. No. 4,013,475, which represents the closest prior art known to applicants, although in an unrelated field, there is described a double emulsion wax polish for treating hard surfaces such as wood or metal. This double emulsion composition is a dispersion of an aqueous emulsion of a finely divided (0.1-5 microns) wax material in a continuous phase made up of a small amount of an organopolysiloxane of prescribed viscosity in a large volume of a hydrocarbon solvent of prescribed aniline point and distillation range characteristics (see column 6, lines 19 et seq). The particulate wax/water emulsion is dispersed in the organopolisiloxane/hydrocarbon solvent phase by means of a non-silicone type of water-in-oil emulsifier (see column 7, lines 14 et seq). Such wax polishing emulsions, however, have obvious disadvantages for cosmetic usage. For one thing, the hydrocarbon solvent is contraindicated for skin applications due to its inherent skin-drying characteristic, indeed skin-damaging upon prolonged contact. For another, the polishing waxes are inherently water resistant and form non-permeable films, which characteristics, although suitable for application to hard surfaces such as wood or metal, are undesirable in skin care compositions. The wax polishing emulsions of U.S. Pat. 4,013,475, therefore, teach away from the skin moisturizing o/w/s multiple emulsion compositions of the subject invention which form non-occlusive, air- and moisture-permeable films upon application to the skin.

DESCRIPTION OF THE INVENTION

It has now been found that a skin moisturizing multiphase emulsion composition may be provided wherein the continuous phase consists essentially of a silicone fluid component and, in addition, an effective dispersing amount of a particular silicone fluid, namely, dimethicone copolyol, is used to disperse in said continuous phase an oil-in-water (o/w) emulsion as the aqueous discontinuous phase, the oil phase of said o/w emulsion being a liquid non-particulate containing material.

More particularly, the subject invention provides an oil-in-water-in silicone fluid (o/w/s) emulsion composition comprising three essential components, namely, a silicone fluid component as the continuous phase, an oil-in-water (o/w) emulsion as the discontinuous phase, and dimethicone copolyol as the dispersing agent, said three components being present in the indicated approximate relative percent by weight proportions:

| Component | % w/w |
|---|---|
| Silicone fluid continuous phase | 15-70 |
| o/w Emulsion discontinuous phase | 30-80 |
| Dimethicone copolyol dispersant | 0.5-5 |

The silicone fluid continuous phase in the subject multiphase emulsion composition consists essentially of at least one liquid organopolysiloxane such as, for example, a volatile silicone fluid, for example, octamethylcyclotetrasiloxane, decamethylcyclopentasiloxane, dodecamethylcyclohexasiloxane, hexamethyldisiloxane and the like, and a non-volatile silicone fluid such as, for example, dimethicone copolyol, dimethylpolysiloxane, diethylpolysiloxane, mixed $C_1$-$C_3$ alkyl (e.g., methyl-ethyl) polysiloxane, phenyl dimethicone and high molecular weight dimethicones (average molecular weight from about 200,000 to about 1,000,000 and, preferably, from about 300,000 to about 600,000) which may have various end-terminating groups such as hydroxy, lower $C_{1-3}$ alkyl, lower $C_1$-$C_3$ alkoxy and the like. In accordance with a preferred embodiment, the silicone fluid continuous phase consists essentially of one or more volatile silicone fluids, preferably cyclomethicone, in admixture with one or more non- volatile silicone fluids in a respective weight ratio (volatile : non-volatile) of from about 5:1 to about 25:1 and, most preferably, from about 10:1 to about 20:1. The term "volatile" is meant to include liquid lower molecular weight organopolysiloxanes having a viscosity of from about 0.65 to about 5 centistokes at 25° C.; and "nonvolatile" meaning higher molecular weight liquid organopolysiloxanes having a viscosity higher than 5.

Liquid organopolysiloxane, also known as silicone fluids, are well known and available from various commercial suppliers. For example, several such silicone fluids are distributed by the Dow Corning Corporation, Midland, Mich., under the following designations: DC 344 Fluid, the volatile cyclomethicone; DC 3225C Fluid, a 90:10 w/w mixture of cyclomethicone and dimethicone copolyol; DC X2-1401 Fluid, a 13:87 w/w mixture of dimethiconol (hydroxy- terminated dimethicone) and cyclomethicone; and DC 556 Fluid, the non-volatile phenyl dimethicone; by The General Electric Company, Silicone Products Division, Waterford, N.Y., under its "SF" designation, for example, SF-96 for dimethicone; and SF-1173 for cyclomethicone; and by Union Carbide Corporation under its "Silicone L" series, for example, Silicone L-45 for dimethicone; and Silicone L-720 for dimethicone copolyol.

The silicone fluid continuous phase is employed in amounts ranging from about 15 to about 70 percent and, preferably, from about 18 to about 40 percent, by weight of the subject o/w/s multiple emulsion. When dimethicone copolyol constitutes the major or total part of the silicone fluid continuous phase, it also acts as the dispersing agent for the o/w emulsion discontinuous phase.

The discontinuous phase in the subject o/w/s multiple emulsion composition comprises an oil-in-water emulsion of a cosmetically acceptable oily liquid phase dispersed in an aqueous phase, generally with a pH range of about 4–8. The o/w emulsion contains from about 70 to about 99 percent and, preferably, from about 85 to about 95 percent, by weight of an aqueous continuous phase, from about 0.5 to about 25 percent and, preferably, from about 2 to about 18 percent, by weight of an oil discontinuous phase, and from about 0.5 to about 5 percent and, preferably, from about 1 to about 2 percent, by weight of a suitable oil-in-water emulsifier.

The aqueous continuous phase of the o/w emulsion may be simply water or water containing one or more soluble or dispersible cosmetically acceptable ingredients. Typical such ingredients include, for example, an emulsifier with a hyprophile-lipophile balance (HLB) value from about 12 to about 20 or even higher such as sodium alkyl polyether sulfonate, polysorbate 20, polysorbate 80, polyoxyethylene 23 lauryl ether, oleth-20 and the like; a humectant such as glycerin, polyethylene glycol, pantethine and the like; a thickener such as an acrylic acid polymer denoted by the Cosmetic, Toiletry & Fragrance Association (CTFA) name "Carbomer", a natural or synthetic gum, a cellulosic derivative and the like; a preservative or antioxidant such as methyl or propyl paraben, butylated hydroxytoluene, butylated hydroxyanisole and the like; and other water soluble additives such as a water soluble sunscreening agent, e.g., ethyl dihydroxypropyl PABA, a water soluble vitamin, e.g., vitamin C, a water soluble colorant, an electrolyte, and the like. In general, the aqueous continuous phase may contain from about 0.5 to about 15 percent by weight of such optional additives.

The oil discontinuous phase of the o/w emulsion may be simply a cosmetically acceptable oil or such oil containing one or more soluble or miscible additives generally used in cosmetic compositions. Typical such oils, also known as emollients, include mineral oil (heavy preferred), squalane, a vegetable oil such as sesame oil, safflower oil, castor oil, avocado oil and the like liquid non-wax oils. Typical oil-soluble or oil-miscible additives include, for example, a fatty ($C_{12}$–$C_{18}$ preferred) acid, alcohol or ester such as myristic acid, palmitic acid, lauric acid, stearic acid, cetyl alcohol, stearyl alcohol, cetyl palmitate, octyl hydroxystearate and the like, a sterol such as cholesterol and other sterol derivatives; and a natural or synthetic wax such as beeswax, spermacetti and the like; skin penetration enhancers such as $C_8$–$C_{10}$ triglycerides; and such other additives as oil soluble vitamins, antioxidants, preservatives, auxilliary emulsifiers and the like. The oil discontinuous phase, which may contain from about 0.5 to about 10 percent by weight of such optional additives, is prepared such that it is void of particulate matter. For example, with the optional wax additive, very small amounts are utilized in relation to the higher amount of solubilizing oil so that no particulate wax material is present in the oil phase. A particularly preferred embodiment of the oil phase comprises heavy mineral oil (0.885–0.895 specific gravity at 25° C.), cholesterol and cetyl palmitate in a respective weight ratio of about 10:5:1.

The oil-in-water emulsion is readily prepared by first thoroughly combining all the water-phase components and all the oil-phase components, including the essential emulsifying agent or agents, in separate vessels at elevated temperatures of about 60°–90° C. In general, the heated oil phase is then slowly added to the heated water phase using moderate to high speed mechanical dispersing means until a uniform o/w emulsion is obtained.

In making the oil-in-water emulsion, it is of an appropriate emulsifier which may be in the water and/or oil phase. It is of course understood that blends of emulsifiers of varying HLB values can be used to obtain the desired HLB value as determinable in the manner described in "The Atlas HLB System" (4th printing) copyright 1963 by Atlas Chemical Industries, Inc., Wilmington, Del. The emulsifier should have a hydrophile-lipophile balance such that the oil component is dispersed in the aqueous medium, generally an HLB value of not more than 14 and, preferably, from about 4 to about 12. Typical emulsifiers are such nonionic and anionic surfactants as polyoxyethylene 20 sorbitan trioleate (Polysorbate 85), sorbitan monolaurate, polyoxyethylene 4 lauryl ether sodium stearate and the like.

The multiphase oil-in-water-in-silicone fluid (o/w/s) emulsion compositions of this invention are readily prepared by using art-recognized principles and methodologies in mixing the ingredients together and in choosing the type of mixing or dispersing equipment to be used. The following Examples provide a general listing of both essential and optional components and illustrate procedures for making the subject compositions.

In general, an effective dispersing amount of dimethicone copolyol is dissolved in the silicone fluid component and then the separately prepared oil-in-water emulsion is added and dispersed, for example, by mechanical dispersing means, into the silicone fluid phase at room temperature to obtain a homogeneous dispersion of the o/w emulsion therein. The dimethicone copolyol dispersant maintains the o/w emulsion as the dispersed phase, also known as the discontinuous phase, in the silicone fluid continuous phase. Stable o/w/s emulsions having various dispersed phase volumes are easily and consistently prepared with high reproducibility. From about 0.5 to about 5 percent and, preferably, from about 1 to about 3 percent, by weight of the dimethicone copolyol dispersant may be advantageously utilized. As noted previously, dimethicone copolyol may also constitute all or part of the silicone fluid continuous phase component of the o/w/s multiple emulsion composition and may act both as the silicone fluid and the dispersant essential components of this invention. By varying the percentage of the essential components, the amounts and types of optional additives, and the shearing effect obtained from the mixing speed and time, the o/w/s multiple emulsion can be obtained in varying viscosity ranges from lotion to heavy cream form.

The subject o/w/s multiple emulsion is effective as a skin care cosmetic composition, in that it provides beneficial moisturizing activity when applied to human skin, particularly to skin cosmetically characterized as dry skin, chapped skin or rough skin. In addition, it is effective as a fundamental form for cosmetics such as lotions and creams which, in addition to providing said moisturizing action to the skin, may also provide other cosmetically desirable properties by incorporation of one or more skin care ingredients possessing a particular cosmetic characteristic, for example, sunscreening or sunblocking agents (a preferred embodiment), skin conditioners, cosmetic pigments and the like. As noted previously, for example, each of the oil and water phases of the o/w emulsion may contain optional cosmetic additives. Similarly, the silicone fluid component may also be utilized as a carrier of optional silicone miscible cosmetically acceptable additives. Typical of such additives are silicone treated pigments and talcs; ultraviolet (U.V.) absorbers for sunscreening or sunblocking protection such as octyl methoxycinnamate, benzophenone-3, silicone treated titanium dioxide and the like; polymeric skin conditioners such as, for example, the commercially available Dow Corning® QF1-593A Fluid, a mixture of dimethyl and trimethyl polysiloxane (Dow Corning Corporation, Midland, Mich.), solubilizers for U.V. absorbers or fragrances such as, for example, $C_{12}$-$C_{15}$ alcohol benzoates; and the like. The subject o/w/s multiple emulsion may also be used as an effective carrier for various medicaments and drugs intended for topical skin application. For example, water soluble drugs may be incorporated into the aqueous phase of the o/w emulsion, oil soluble or oil miscible drugs may be incorporated into the oil phase of the o/w emulsion, and silicone treated or silicone miscible drugs may be incorporated into the silicone fluid component.

The following examples are intended to illustrate, but not to limit, the subject invention.

EXAMPLE I Part 1

An o/w emulsion is prepared from the following ingredients, identified by chemical or CTFA name. The indicated % w/w is based on the total weight of the finally prepared o/w/s multiple emulsion.

| Ingredient | % w/w |
| --- | --- |
| Aqueous Phase: | |
| Purified water | 64.85 |
| Sodium alkyl polyether sulfonate, HLB > 12 | 1.50 |
| Carbomer 940 | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.50 |
| Neutralizer Base: | |
| Triethanolamine | 0.10 |
| | 70.00 |

In a suitably sized vessel equipped with a suitable mechanical stirrer, (Tekmar Model RW-20 stirring motor, manufactured by IKA-WERK, Germany), the water and sulfonate emulsifier are heated to about 72°-75° C. and mixed. Stirring is increased until a vortex forms in the aqueous solution. The thickener, Carbomer 940, is slowly added to the vortex and allowed to mix until completely hydrated and the resultant gel solution is free of gelatinous particles and is uniform in composition. The temperature is maintained at about 72°-75° C. with constant agitation.

The oil phase ingredients are added to a separate suitably sized vessel and heated to about 80°-85° C. using slow mechanical stirring once the oil phase becomes molten. When molten, agitation is maintained to keep the oil phase unform during heating.

The heated oil phase is then slowly added to the heated water phase with stirring to form the o/w emulsion. After addition is complete, the mechanical dispersing means is slowed to avoid unnecessary aeration of the emulsion and mixing is continued for approximately fifteen minutes at 70°-75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous o/w emulsion is then cooled to room temperature (about 25° C.) with continued moderate agitation.

| Part 2: | |
| --- | --- |
| Ingredient | % w/w |
| Silicone fluid phase: | |
| Cyclomethicone | 15.00 |
| Dimethicone Copolyol in Cyclomethicone (10:90) | 15.00 |
| | 30.00 |

The silicone fluid phase ingredients are added to and mixed in a suitable sized vessel equipped with mechanical dispersing means at 25° C. until a uniform solution is attained. The o/w emulsion of Part 1 at 25° C. is then slowly added to the silicone fluid phase with slow mechanical stirring during addition to maintain the integrity of the double emulsion system. When addition is complete, mechanical stirring may be increased slightly in order to achieve complete uniformity and consistency of the final o/w/s multiple emulsion in lotion form.

The lotion emulsion of this example is rubbed on the skin in the conventional manner for applying cosmetic skin lotions, leaving the skin with a coating that moisturizes and softens the skin.

EXAMPLE II

In this example, a moisturizing o/w/s sunscreen emulsion lotion is formed from the following ingredients (indicated by chemical or CTFA name).

| Ingredient | % w/w |
| --- | --- |
| Aqueous Phase: | |
| Purified water | 61.17 |
| Pantethine, 80% aq. soln. (humectant) | 0.10 |
| Methylparaben (preservative) | 0.20 |
| Carbomer 940 (thickener) | 0.10 |
| Glycerin (humectant) | 2.50 |
| Sodium alkyl polyether sulfonate (anionic emulsifier) | 1.25 |
| Oil Phase: | |
| Heavy mineral oil | 1.75 |
| Cholesterol (emollient & aux. emuls.) | 1.00 |
| Cetyl palmitate (aux. emuls.) | 0.20 |
| PEG-22/Dodecyl glycol copolymer (emuls.) | 0.20 |
| Ethylparaben (preservative) | 0.10 |
| Propylparaben (preservative) | 0.15 |
| Neutralizer Base: | |
| Triethanolamine | 0.10 |
| Color & Fragrance: | |
| FD&C Red No. 4 (1% aq. soln.) | 0.03 |
| Odorant oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (aux. emuls.) | 2.00 |
| Octyl Methoxycinnamate (U.V.-absorber) | 7.00 |
| Benzophenone-3 (U.V.-absorber) | 0.50 |
| $C_{12-15}$ Alcohols Benzoate (solubilizer) | 2.85 |

| -continued | |
|---|---|
| Ingredient | % w/w |
| | 100.00 |

The aqueous phase ingredients other than the Carbomer 940 thickener are heated and mixed together followed by addition of the Carbomer 940 as in Example I and maintained at about 72°–75° C. with constant agitation. The oil phase ingredients are mixed together in a separate vessel and maintained at about 80°–85° C. The heated oil phase is then slowly added to the heated water phase, as in Example I, to form the o/w emulsion (about 70°–75° C.). After neutralization of the Carbomer 940 by addition of the triethanolamine (about 60° C.), the emulsion is further cooled with continued moderate mixing and the colorant (about 45°–50° C.) and odorant oil (about 35°–40° C.) are added, followed by cooling to room temperature (about 25° C.).

The four silicone fluids and other silicone phase ingredients are mixed together in a separate vessel until a uniform silicone phase is attained. The o/w emulsion is slowly added to the silicone phase with stirring until a homogeneous o/w/s double emulsion in lotion form is attained.

Upon conventional application to skin areas, the emulsion lotion leaves the skin with a coating that, in addition to providing sun-protective activity, moisturizes and softens the skin.

We claim:

1. An oil-in-water-in-silicon fluid emulsion composition comprising (a) from about 15% to about 70% weight of a silicone fluid continuous phase consisting essentially of at least one liquid organopolysiloxane; (b) from about 30% to about 80% by weight of an aqueous discontinuous phase comprising an oil-in-water emulsion of a cosmetically acceptable oily liquid non-particulate phase dispersed in an aqueous phase; and (c) from about 0.5% to about 5% by weight of an effective dispersing amount of dimethicone copolyol for dispersing (b) in (a).

2. The composition of claim 1 wherein said liquid organopolysiloxane is a volatile organopolysiloxane selected from the group consisting of octamethylcyclotetrasiloxane, decamethylcyclopentasiloxane, dodecamethylcyclohexasiloxane and hexamethyldisiloxane.

3. The composition of claim 1 wherein said liquid organopolysiloxane is a non-volatile organopolysiloxane selected from the group consisting of dimethylpolysiloxane, diethylpolysiloxane, mixed $C_1$–$C_3$ alkyl polysiloxane, phenyl dimethicone, dimethiconol and a high molecular weight dimethicone having an average molecular weight of from about 200,000 to about 1,000,000.

4. The composition of claim 1 wherein said silicone fluid continuous phase consists essentially of one or more volatile organopolysiloxanes in admixture with one or more non-volatile organopolysiloxanes in a respective weight ratio of from about 5:1 to about 25:1.

5. The composition of claim 4 wherein said volatile organopolysiloxane is cyclomethicone.

6. The composition of claim 1 wherein the oily liquid phase of (b) comprises heavy mineral oil, cholesterol and cetyl palmitate in a respective weight ratio of about 10:5:1.

* * * * *

UNITED STATES PATENT OFFICE
CERTIFICATE OF CORRECTION

PATENT NO. : 4,960,764
DATED : October 2, 1990
INVENTOR(S) : Figueroa, Jr., et al.

It is certified that error appears in the above-identified patent and that said Letters Patent is hereby corrected as shown below:

Column 1, line 9, after "(i.e.," and before "moisturizing" insert
-- double) emulsion composition having excellent skin --.

Column 4, line 10, after "is" and before "of" insert -- necessary to utilize an effective emulsifying amount --.

Signed and Sealed this

Third Day of March, 1992

Attest:

HARRY F. MANBECK, JR.

*Attesting Officer*   *Commissioner of Patents and Trademarks*